United States Patent [19]
Bernreuter

[11] Patent Number: 5,922,607
[45] Date of Patent: *Jul. 13, 1999

[54] MEASURING PROCESS FOR BLOOD GAS ANALYSIS SENSORS

[76] Inventor: Peter Bernreuter, Unterleinsiedl 4, D-92289 Ursensollen, Germany

[ * ] Notice: This patent is subject to a terminal disclaimer.

[21] Appl. No.: 08/763,850

[22] Filed: Dec. 11, 1996

[30] Foreign Application Priority Data

Dec. 13, 1995 [DE] Germany .................. 195 46 502

[51] Int. Cl.⁶ .................... G01N 33/50; G01N 21/00; G01N 21/75
[52] U.S. Cl. .................. 436/68; 436/164; 436/167; 436/805
[58] Field of Search .................. 436/68, 501, 805, 436/164, 167, 171

Primary Examiner—Bradley L. Sisson
Attorney, Agent, or Firm—Dennison, Meserole, Scheiner & Schultz

[57] ABSTRACT

The invention relates to a measuring process, the purpose of which is to increase the measuring accuracy of pulse oxymeters and comparable optical devices which are used in vivo to ascertain oxygen saturation of arterial blood. The measuring process according to the invention is provided for the purpose of ascertaining oxygenation of arterial blood in tissue by evaluating the differential light attenuation at several wavelengths. It is characterized by the fact that light attenuation of at least one wavelength is determined in order to choose those calibration curves of several variables ($\Omega_1$, $\Omega_2$. . . .) produced by different wavelength pairings with a minimized error in order to generate an output signal for the arterial blood oxygenation.

16 Claims, 2 Drawing Sheets

MEASURING PROCESS FOR BLOOD GAS ANALYSIS SENSORS

BACKGROUND OF THE INVENTION

The invention relates to a measuring process, the purpose of which is to increase the measuring accuracy of pulse oxymeters and comparable optical devices which are used in vivo to ascertain oxygen saturation of arterial blood.

According to the current prior art pulse oxymeters function on the basis that differing wavelengths blood attenuates light very differently depending upon the level of oxygenation. Pulse waves starting from the heart cause in the arterial blood vessel system a periodic fluctuation in the arterial blood content in the tissue. As a consequence, a periodic change in the light absorption (FIG. 1) can be registered between the light transmitter, whose radiation passes through the tissue, and the receivers, which are integrated in a pulse oxymetry sensor. The evaluation of the sensor signals is normally carried out at light wavelength of 660 and 940 nm by calculating the differential change of light absorption. It is possible to create a measured variable $\Omega$ (sometimes also referred to as R) which is obtained in the following manner or in a similar manner:

$$\Omega = \frac{\ln \frac{I_{min\lambda 1}}{I_{max\lambda 1}}}{\ln \frac{I_{min\lambda 2}}{I_{max\lambda 2}}}$$

The light intensities described in the formula represent the light intensities received in the receiver of the sensors used in pulse oxymetry. The measured variable $\Omega$ serves as a measurement for the oxygen saturation. The formation of a quotient in order to form the measured variable is intended to compensate for any possible influences the haemoglobin content of the tissue, the pigmentation of the skin or the pilosity may have on the measurement of the oxygen saturation of arterial blood. (See also "Biomedizinische Technik" [Biomedical Technology] Volume 33, Supplementary volume 3, page 6 ff.:"Pulse oxymetrie: Stand und Entwicklung der Technik" "Pulse oxymtery: Status and development of the technology"; Volume 35, Supplementary volume 1, page 38 ff. "Pulsoxymetrie" [Pulse oxymetry] by K Fortsner Institute for Biomedical Technology, Stuttgart). The influences of blood perfusion in the tissue, the pigmentation and pilosity are not taken into consideration in this measuring process.

When measuring oxygen saturation of arterial blood in the tissue in a range of 70 to 100% using light of wavelength 940 nm and 660 nm sufficiently accurate measured values are produced. However, in order to measure lower oxygen saturation of arterial blood it is necessary to assume a strong influence on the measured variable $\Omega$ in particular caused by perfusion (i.e. blood content) (see: IEEE Photon Diffusion Analysis of the Effects of Multiple Scattering on Pulse Oximetry by Joseph M. Schmitt) and other optical parameters of tissue.

The dependency of the oxygen saturation of arterial blood $SaO_2$ on the variable $\Omega$ and the perfusion p can be written as follows (see also FIG. 2):

$SaO_2 = f(\Omega, p)$

Similar influences can be caused by pigmentation and pilosity of the skin or scattering and inhomogeneous tissue.

SUMMARY OF THE INVENTION

The technical problem resides in the fact that oxygen saturation of arterial blood must be determined in vivo using the process of pulse oxymetry without the perfusion, scattering and inhomogeneity in the tissue or pigmentation and pilosity of the skin influencing the measured result. For this reason, it is necessary to locate from the number of possible calibration curves, those curves which render it possible to determine in the most precise manner the oxygen saturation of arterial blood.

This problem is achieved in accordance with the invention, by measuring the light attenuation LA in the tissue, which can be determined by relating the intensity I registered in the receiver of the sensor to the initial intensity $I_0$ generated by the emitter for at least one wavelength. It possible to select from a number of possible calibration curves those curves with which the oxygen saturation of the arterial blood can be determined in the most precise manner possible to improve considerably the accuracy of the measured values using pulse oxymeters particularly in cases where the oxygen saturation of the blood is low. (Note: In this context "attenuation" means, that there is a defined relation between $I(t)$ and $I_0(t)$).

A further solution in accordance with the invention for the purpose of minimizing the error in the measured values, resides in the fact that the measured value error can be minimized by measuring variables which are obtained from different wavelength pairings. Special choice of wavelength pairings allows to measure additional optical parameters if the calibration curve of this wavelength pairing is very sensitve to changes of the said parameter. Thus the best fitting calibration curves of wavelength pairings which are more sensitive to arterial oxygen changes can be chosen in order to determine the oxygen saturation.

A further solution to avoid the dependencies of measuring arterial saturation upon pilosity and pigmentation of the skin measures these parameters are measured by determination of the attenuation between a receiver and emitter of light, which are close to one another (optical unit) (FIG. 4). By measuring the attenuation within further optical units and between these optical units optical parameters of the tissue can be determined without the influence of the said parameters.

In a further aspect of the invention, measuring arterial oxygenation is accomplished by concurrently measuring the electrical activity of the subject whose blood oxygenation is determined in order to detect arte facts while registering the differential attenuation of blood.

The error is minimized by characterising the tissue inhomogeneity. This can be done by comparing the differential light absorptions.

$$\frac{I_{min\lambda 1}}{I_{max\lambda 1}}$$

at different distances of the light receivers and emitters.

DESCRIPTION OF THE PREFERRED EMBODIMENTS

Figure 1:
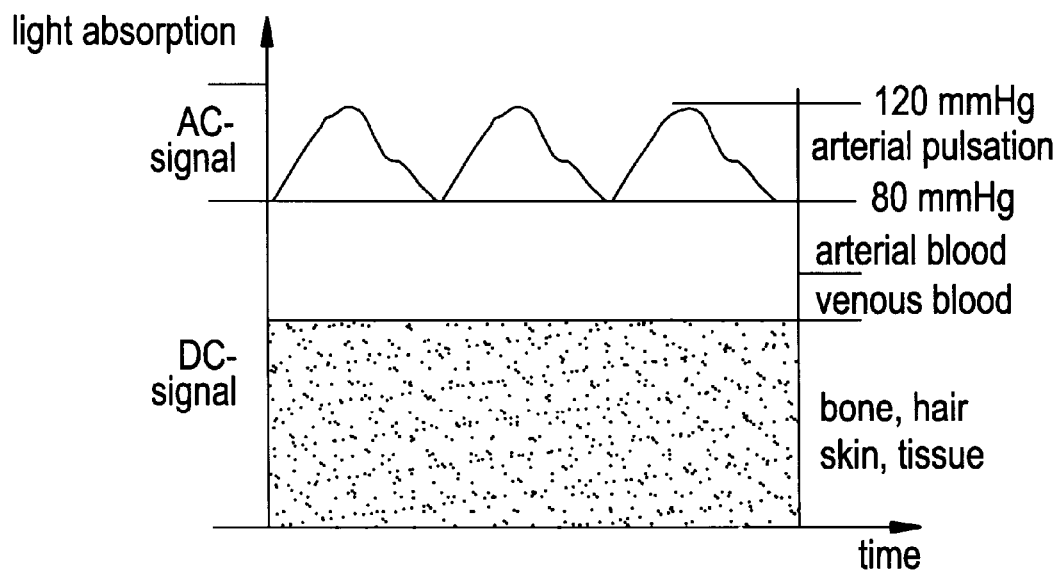
FIG. 1 is a graph illustrating the change of light absorption with time.

The diagram of FIG. 1 shows the fundamental effect, on which pulse oxymetry and comparable methods to determine arterial blood oxygenation are based. When measuring light absorption of tissue in vivo light absorption changes synchronously with every heart cycle. The diagram illustrates the change of light absorption versus time, which is caused by arterial pulsations that can be measured during systole and diastole. During systole and diastole the pressure on the arterial vessel system varies from 80 mmHg to 120 mmHg. The change of light absorption is called the AC signal. The DC signal, the time-invariant part of the light absorption, is caused by the non-pulsating part of the arterial blood, the venous blood, bone hair, skin, tissue and other constant absorbers versus time.

Figure 2:
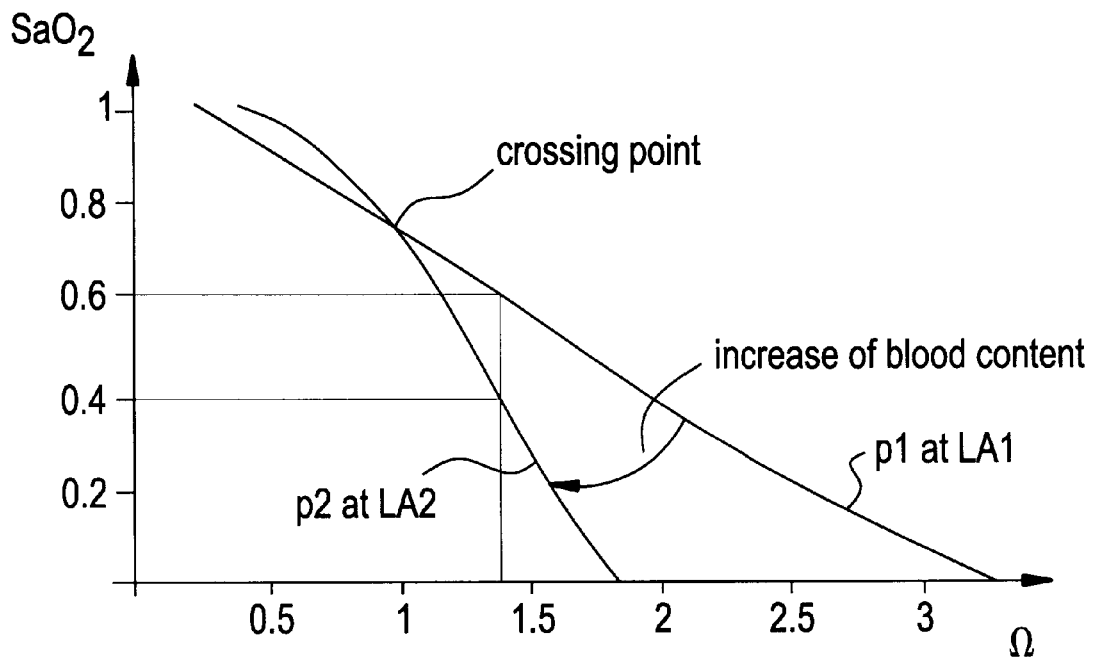
FIG. 2 is a graph illustrating the despendency of oxygen saturation of arterial blood.

FIG. 2 shows two calibration curves in a diagram with $SaO_2$ vs. $\Omega$. One diagram is marked with the label "p1 at LA1". This means that this calibration curve is only valid for a special level of perfusion (blood content) which can be measured with an optical system. The optical system can measure the light attenuation LA1 which is equivalent to perfusion p1. The second calibration curve is characterized by the perfusion p2 at LA2. The arrow between these two calibration curves indicates how the curves change their shape when perfusion increases. There is one point where $SaO_2$ is independent of perfusion, that is the crossing point. Additionally there are dotted lines in the diagram at $SaO_2$= 0.6, $SaO_2$=0.38 and $\Omega$=1.4. If an optical system determines only $\Omega$ without registering the light attenuation, this would result in a maximum error of 0.224 $SaO_2$ ($SaO_2$ at p1—$SaO_2$ at p1 with $\Omega$=1.4).

Figure 3:
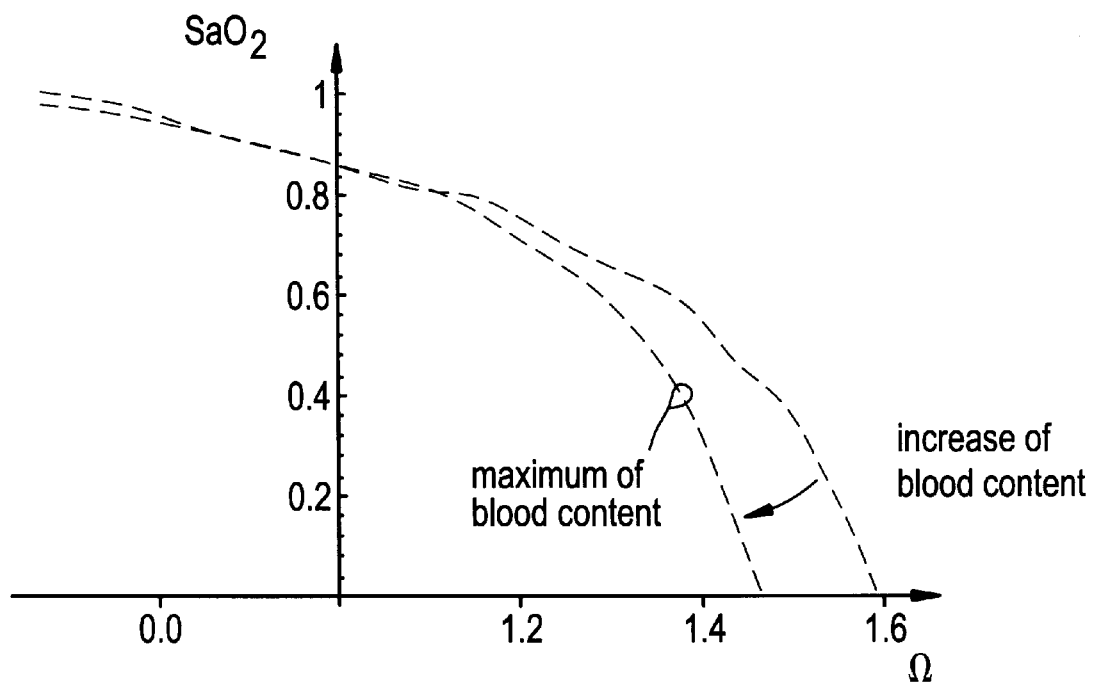
FIG. 3 shows two calibration curves ($SaO_2$ vs. $\Omega$)

FIG. 3 shows two calibration curves which depend on blood content of tissue. The arrow shows how curves will change when blood content increases. $\Omega$ is evaluated in this example from the wavelengths 730 nm and 660 nm. When $SaO_2$ is below 0.5 the calibration curves depend on changes of blood content rather than on changes of $SaO_2$. This effect can be used to measure blood content in tissue in order to choose the calibration curve of warelength pairings with a minimum of error of $SaO_2$.

Figure 4:
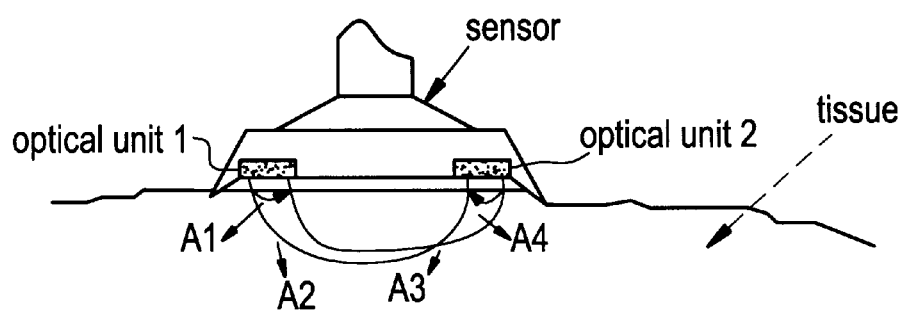
FIG. 4 shows a pulse oxymetry sensor according to the invention.

FIG. 4 shows a pulse oxymetry sensor on the upper part of the figure which is placed on tissue. The sensor contains two optical units which consist of a light emitter and receiver. The arrows A1, . . . , A4 show how light passes from light emitters to detectors through tissue. A1 stands representative for light, which is emitted in the optical unit 1 and detected in unit 1. A2 is emitted in optical unit 1 one and detected in unit 2. A4 is emitted in unit 2 and detected in unit 2 and A3 is emitted in unit 2 and detected in unit 1.

EXAMPLE 1

Arterial oxygenation of blood in tissue depends on different optical parameters. FIG. 2 shows how calibration curves change, when blood content increases for a special wavelength pairing (660 nm and 940 nm, qualitatively).

After light attenuation, which corresponds to different blood contents in the tissue is determined, the calibration curve with the minimal error is chosen. This means—if the measured light attenuation is LA1 and the $\Omega$ is 1.4—the output signal for $SaO_2$ is 0.6 and not 0.38 for the calibration curve at LA2.

EXAMPLE 2

FIG. 3 shows a diagram with a pairing of wavelength (730 nm and 660 nm), whose calibration curves depend on optical parameters of tissue (here blood content) but not on the arterial oxygenation for $SaO_2$ values below 50%. This effect is used to choose the calibration curve of a second wavelength pairing (see FIG. 2) with the minimal error for oxygenations. This means that if the estimation of a wavelength pairing for $SaO_2$ produces an output of $SaO_2$=0.30 and $\Omega$ for the calibration curves in FIG. 3 is 1.4, that blood content in tissue must be at a maximum. Therefore the calibration curve for the maximum of blood content will be chosen.

EXAMPLE 3

In order to exclude the influence of pilosity an pigmentation, while determining optical parameters of tissue all light attenuations A1, . . . , A4 (see FIG. 4) between the two optical units are determined.

The light attenuation LA of the tissue alone could be calculated as follows:

$$LA=(A2+A3-A1-A4)/2$$

This correlation is also very helpful to detect haematoms, which could increase the error of the output variable $SaO_2$.

What is claimed is:

1. A method of determining the level of oxygenation of arterial blood $SaO_2$ in tissue in vivo considering optical tissue properties by pulse oximetry, comprising the steps of:
   a) emitting light through said tissue at a plurality of wavelengths at different instants of time, and different resultant blood flow;
   b) measuring said light received passing through said tissue at said plurality of wavelengths at said instants of time;
   c) calculating a plurality of ratios of differential attenuation vs. time, $\Omega_i$ which can be calculated as $$\Omega_1 = \frac{\ln(i_{min}/i_{max})_a}{\ln(i_{min}/i_{max})_b}$$

for each wavelength pair i=a,b of different frequencies;
   d) calculating at least one attenuation ratio $LA_j$ through said tissue for at least one wavelength where $LA_j$ can be calculated as: $LA_j$=ln (light intensity received/light intensity emitted);
   e) obtaining calibration data of $SaO_2$ v. $\Omega_i$ for at least one frequency for each said $LA_j$;
   f) computing the level of oxygenation depending by comparing measured data with the calibration data.

2. The method of claim 1, additionally comprising calculating $\Omega_1$ as:

$$\Omega_i = \frac{\frac{\text{change of intensity at freq. } a}{\text{total light intensity at freq. } a}}{\frac{\text{change of intensity at freq. } b}{\text{total light intensity at freq. } b}}$$

3. The method of claim 1 wherein in step c), at least one wavelength pairing is selected based on optical tissue parameters, sufficient wavelength pairings and calibration curves of SaO2 v. $\Omega_i$ are empirically made such that the calibration curves are chosen for $\Omega_i$ depending on optical tissue parameters to minimize error in producing an output signal indicative of level of arterial oxygenation.

4. The method of claim 3, wherein the wavelength pairings are 660 and 940 nm or 730 and 940 nm.

5. The method of claim 1, wherein at least two emitter/detector pairs are utilized, comprising the steps of:

g) measuring light emitted in a first optical unit and detected in a first optical unit;

h) measuring light emitted in said first optical unit and detected in a second optical unit;

i) measuring light emitted in said second optical unit and detected in said first optical unit;

j) measuring light emitted in said second optical unit and detected in said second optical unit;

k) weighting light attenuations between detectors and emitters to generate LA;

l) repeating steps g)-k) for more than two optical units and weighting generated values of LA in order to generate a resulting light attenuation;

m) using the determined light attenuation to choose an associated calibration curve.

6. The method of claim 1, wherein the step of determining differential attenuation vs. time is accompanied by a concurrent measurement of electrical activity of the heart.

7. The method of claim 1, wherein at least two emitter/detector optical units are utilized, comprising the steps of:

n) measuring light emitted in a first optical unit and detected in said first optical unit A1;

o) measuring light emitted in said first optical unit and detected in a second optical unit A2;

p) measuring light emitted in said second optical unit and detected in said first optical unit A3;

q) measuring light emitted in said second optical unit and detected in said second optical unit A4;

r) computing the optical constitution of said tissue alone relating to the measured light attenuation by weighting and accumulating the light attenuations between the optical units (A2, A3) and subtracting therefrom the weighted and accumulated light attenuations within the optical units (A1, A4); and s) repeating steps n)-r) for any other sets of optical unit pairs, and an appropriate weighting in accordance with step r);

t) generating an output signal for the arterial oxygen saturation depending on LA or a set of LA values.

8. The method of claim 7, wherein light attenuation is defined as $A_k = \ln$ (light intensity).

9. The method of claim 7, additionally comprising using the data generated in step r) to prepare calibration curves, and computing the level of oxygenation by obtaining the data from the calibration curves.

10. The method of claim 1, wherein tissue inhomogeneity $LAT_m$ is evaluated by measuring:

u) differential attenuation, $dLA_j$, at a first distance between emitter and detector;

v) differential attenuation, $dLA_k$, at a second distance between emitter and detector;

w) calculating $LAT_m = dLA_j/dLA_k$;

x) repeating steps u)-x) for further pairs of emitter/detector distances;

y) generating an output signal for the arterial oxygen saturation depending on $LAT_m$.

11. The method of claim 10, wherein the differential attenuation is defined as:

dLA=light intensity change at distance j within time light intensity change at distance k within time interval $\Delta t$ change in light absorption at a distance j,k within a time interval $\Delta t$.

12. The method of claim 10, additionally comprising using the data generated in step w) to prepare calibration curves, and computing the level of oxygenation by obtaining the data from the calibration curves.

13. The method of claim 11, wherein said attenuation ratio $LA_j$ is calculated as:

$$LA_j = \ln \frac{\text{light intensity received}}{\text{light intensity emitted}}$$

14. The method of claim 11, wherein $LA_j$ depends on change of light intensity versus time emitted by at least one emitter $I_n(t)$ and on change of light intensity received by at least one receiver $I(t)$ which receives the light of said at least one emitter.

15. The method of claim 1, additionally comprising using the data generated in step e) to prepare calibration curves, and computing the level of oxygenation by obtaining the data from the calibration curves.

16. The method of claim 1 wherein in step c), an output signal indicative of level of arterial oxygenation is generated by an additional step comprising selecting a function which depends on $\Omega$ values based on optical tissue parameters, light attenuations and differential light absorptions, and approximates empirical data obtained from calibration curves.

* * * * *

UNITED STATES PATENT AND TRADEMARK OFFICE
CERTIFICATE OF CORRECTION

| | |
|---|---|
| PATENT NO. : 5,922,607 | |
| DATED : July 13, 1999 | |
| INVENTOR(S) : Peter Bernreuter | |

It is certified that error appears in the above-identified patent and that said Letters Patent is hereby corrected as shown below:

<u>Title page,</u>
After "Item [76] Inventor:" correct the inventor information to read as follows:

-- Peter Bernreuter, Gartenstrasse 12, D-73230 Nabern Kirchheim, DE --;

After "Item [30] Foreign Application Priority Data" insert:

-- Jan. 3, 1996 (PCT) EP 96/00003 --

Signed and Sealed this

Fourth Day of December, 2001

*Attest:*

NICHOLAS P. GODICI
*Attesting Officer*  Acting Director of the United States Patent and Trademark Office